United States Patent [19]

Schwartz

[11] Patent Number: 5,720,291
[45] Date of Patent: Feb. 24, 1998

[54] THREE DIMENSIONAL MEDICAL ULTRASONIC DIAGNOSTIC IMAGE OF TISSUE TEXTURE AND VASCULATURE

[75] Inventor: Gary Allen Schwartz, Seattle, Wash.

[73] Assignee: Advanced Technology Laboratories, Inc., Bothell, Wash.

[21] Appl. No.: 638,710

[22] Filed: Apr. 29, 1996

Related U.S. Application Data

[60] Provisional application No. 60/013,951, Mar. 22, 1996.

[51] Int. Cl.$^6$ .......................................... A61B 8/00
[52] U.S. Cl. ........................... 128/661.1; 128/916
[58] Field of Search ................ 128/661.07, 660.04, 128/660.05, 661.08, 661.09, 661.1, 916; 73/861.25

[56] References Cited

U.S. PATENT DOCUMENTS

| | | | |
|---|---|---|---|
| 4,694,434 | 9/1987 | von Ramm et al. | 367/7 |
| 4,794,932 | 1/1989 | Baba | 128/661.09 |
| 5,282,471 | 2/1994 | Sato | 128/660.07 |
| 5,295,486 | 3/1994 | Wollschlager et al. | 128/661.01 |
| 5,329,929 | 7/1994 | Sato | 128/660.65 |
| 5,365,929 | 11/1994 | Peterson | 128/661.1 |
| 5,396,890 | 3/1995 | Weng | 128/660.07 |
| 5,474,073 | 12/1995 | Schwartz et al. | 128/661.1 |
| 5,476,097 | 12/1995 | Robinson | 128/660.05 |
| 5,485,842 | 1/1996 | Quistgaard | 128/66.07 |

OTHER PUBLICATIONS

Three–Dimensional Reconstruction of Echocardiograms Based on Orthogonal Sections, S. Tamura et al., Pattern Recog., (1985) p. 115.

Multidimensional Ultrasonic Imaging for Cardiology, H.A. McCann et al. Proc. IEEE, v. 76, No. 9, (Sep. 1988) pp. 1063–1073.

VoxelView 2.5 User Guide, Vital Images, Inc. (1995), introduction, Chapter 7 & Chapter 10.

V–Buffer: Visible Volume Rendering, by C. Upson et al. in Computer Graphics, vol. 22, No. 4 (Aug. 1988) at pp. 59–64.

Primary Examiner—George Manuel
Attorney, Agent, or Firm—W. Brinton Yorks, Jr.

[57] ABSTRACT

A medical diagnostic ultrasound system is described in which ultrasonic B mode tissue information and Doppler flow information is acquired from a volumetric region of the body and processed together to render a three dimensional image. The three dimensional rendering processes the B mode and Doppler flow information as a function of the spatial location of B mode and Doppler pixels in the volumetric region. The rendering utilizes separate three dimensional rendering parameters for the tissue and flow information, respectively.

19 Claims, 5 Drawing Sheets

THREE DIMENSIONAL MEDICAL ULTRASONIC DIAGNOSTIC IMAGE OF TISSUE TEXTURE AND VASCULATURE

This application is a continuation of provisional application Ser. No. 60/013,951, filed Mar. 22, 1996.

This invention relates to medical ultrasonic diagnostic imaging techniques and, in particular, to the ultrasonic diagnostic imaging of tissue textures and vasculature.

Three dimensional ultrasonic imaging, regarded in the past as a laboratory curiosity, has advanced to commercial reality. The HDI® 3000 diagnostic ultrasound system manufactured by the present inventor's assignee company is the first commercially produced ultrasound system with integrated three dimensional imaging capabilities. The HDI 3000 system utilizes three dimensional Doppler imaging techniques described in U.S. Pat. No. 5,474,073 to produce three dimensional presentations of the blood flow networks of tissue and organs within the body. It does so without the need for additional devices and mechanisms, utilizing only the usual ultrasonic scanhead. Moreover, this system creates its three dimensional blood flow presentations with a conventional planar image scan converter, as more fully described in U.S. Pat. No. 5,485,842.

A significant attribute of the HDI 3000 is its ability to provide three dimensional presentations of blood flow through power Doppler imaging, without the clutter of B mode signals. This technique affords the advantage of automatic segmentation of blood flow information in a three dimensional region of the body. But while the HDI 3000 system is capable of producing exquisite three dimensional presentations of the continuity and intricacies of a network of blood vessels, physicians can at times desire further information on the surrounding tissue and its relationship to the vasculature. For instance, a physician trying to diagnose the development of a fetus may want to determine the viability of the placenta in order to assess fetal nourishment and growth. An important aspect of this inquiry is the vascular structure within the placenta, which in many cases can be easily determined by the three dimensional power Doppler imaging capabilities of the HDI 3000 system. But in cases where the placenta is tightly adjacent to the uterine wall, a presentation of the blood flow network alone may not clearly distinguish between vessels of the placenta and those of the uterus. It is at times like this that the physician would also desire to augment the three dimensional blood flow information with that of the surrounding tissue structure, so that the vascular networks of the two organs can be clearly differentiated.

However, the difficulties in trying to combine three dimensional blood flow information with three dimensional tissue information are legion. U.S. Pat. No. 5,329,929 lists a number of these difficulties. One is the speckle phenomenon inherent in coherent imaging such as ultrasound, which impedes attempts to binarily segment tissue information. This means that the boundaries and outlines cannot be clearly defined, which in turn presents difficulties when employing standard boundary modeling techniques to determine the three dimensional extent of the tissue of different organs.

Second, the disparity in pitch between planes in comparison with the pitch between scanlines in a plane is said to result in a blurred, less dense image in the scanning plane direction.

Third, and most significantly, the display of the tissue or organ surface in three dimensions obscures the internal structure of the object, whereas displaying the interior of the object makes it impossible to visualize its surface. This problem, the '929 patent states, cannot be solved.

Thus, while three dimensional images of both tissue and vasculature would be of considerable benefit and desired by the physician, the obstacles inherent in doing so are acknowledged as being insurmountable. The present invention, however, reveals a new paradigm which lays to rest many of these shibboleths of three dimensional imaging.

In accordance with the principles of the present invention, a technique is provided for producing three dimensional ultrasonic presentations of both tissue and blood flow. A set of three dimensional ultrasonic tissue data and a set of three dimensional ultrasonic blood flow data are acquired from a common region of the body. The data sets are acquired in close time proximity so as to maintain the spatial correspondence of the two data sets. An ultrasonic imaging system includes means for rendering a three dimensional presentation of the combined tissue and blood flow data sets, including means for determining independent three dimensional rendering parameters for the two data sets, such as opacity and contrast weighting. In a preferred embodiment a three dimensional presentation is formed by rendering the combined data sets on a spatial basis, with weighting of the proximity of the data to a viewing plane.

The use of separate parameters for tissue and blood flow, together with the rendering of the combined data sets, yields a presentation in which the opacity of the tissue portions of the three dimensional presentation may be controlled so as to reveal internal structure and vasculature. Moreover, the opacity of the tissue may be controlled to yield clinically discernible textures and boundaries to the tissues being three dimensionally imaged. Thus, in the foregoing example, the tissue texture of the placenta will appear different from that of the more layered texture of the uterine wall. The two different textured volumes can give the physician the structural information necessary to clearly delineate the vasculature of the placenta with its surrounding tissue texture from that of the uterus with its own tissue texture.

Figure 1:
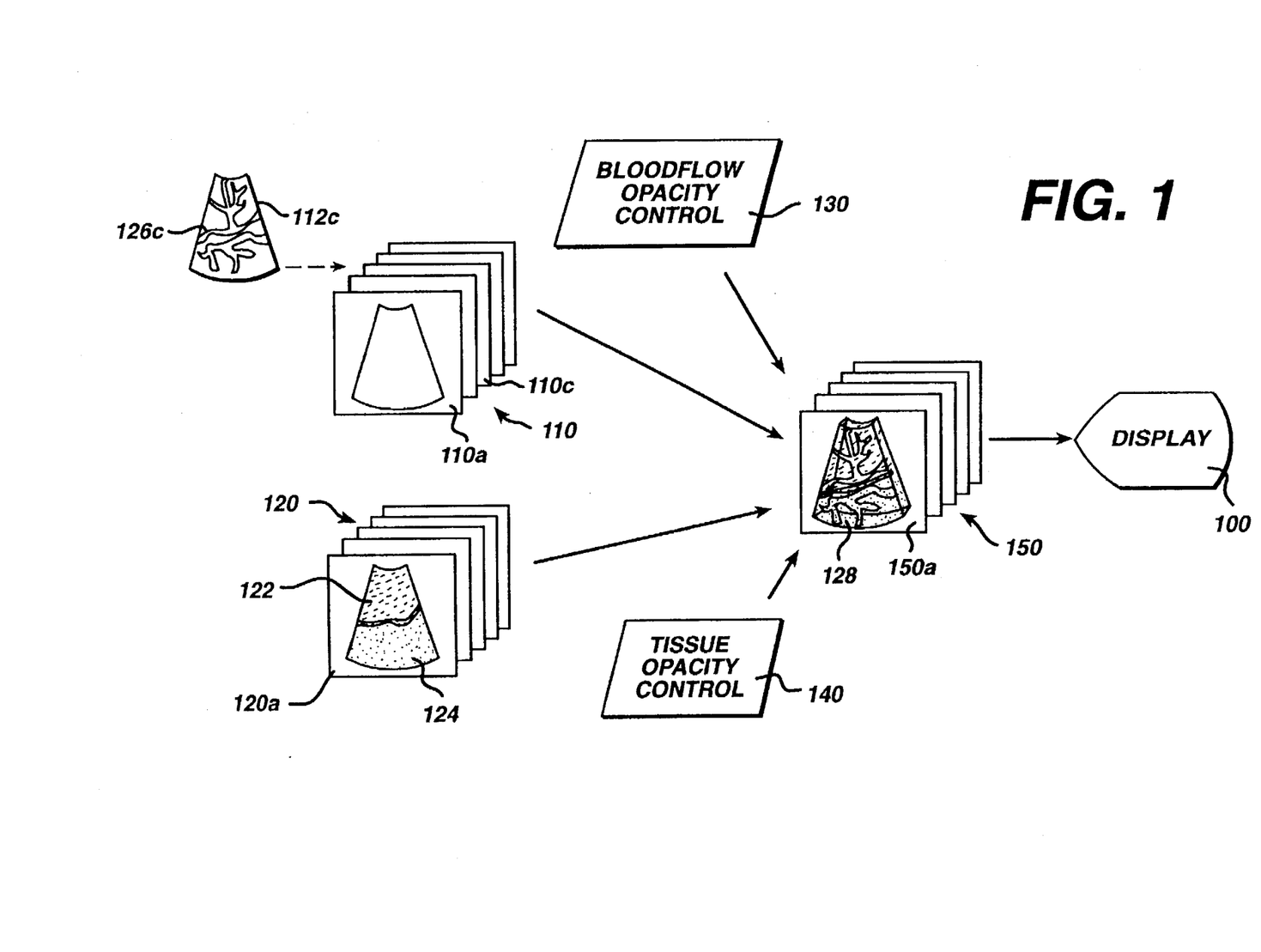
FIG. 1 diagrammatically illustrates the combination of tissue and blood flow ultrasonic image data to render three dimensional images in accordance with the principles of the present invention.

Referring first to FIG. 1, a sequence of ultrasonic blood flow images is shown at 110 and a corresponding sequence of ultrasonic B mode, or tissue images is shown at 120. Each sequence of images is a plurality of planar images taken through different slice planes of a volumetric region of a patient. In this illustration the sequence is in order of depth through the volumetric region; the top image is taken through the front of the region, for instance, and successive images were acquired at progressive depths from the front toward the back of the region.

The images in the blood flow image sequence exhibit close spatial correspondence to images of the tissue image sequence. That is, the position of the flow in the blood flow images corresponds to the position of the blood vessels in the tissue images. This correspondence is most easily achieved by acquiring the image data of both sequences at the same time. This may be done by time interleaving Doppler and B mode line acquisitions or interleaving frames of Doppler information with frames of B mode information, for instance. This spatial correspondence of the two types of image information allows them to be combined in a three dimensional display rendering which accurately depicts the spatial relationship of the tissue and blood flow in the volume from which the images were acquired.

The problem cited by the '929 patent as insoluble is the obscuring of internal structure and blood flow of an organ by the B mode pixels of the surface of the organ. For instance, suppose that the first image 120a of the tissue image sequence depicts tissue of two adjacent organs 122 and 124, in particular, tissue that is closest to the viewer in a three dimensional presentation. Suppose also that image 110c in the interior of the corresponding blood flow image sequence 110 shows a blood flow network in the interior of the two organs, as shown in image frame 112c. The problem seen by the '929 patent is that, when the image sequences are rendered to produce a three dimensional display presentation, the tissue structure of tissue image 120a will be closest to the viewer and hence will obscure the internal blood flow networks 126c of the organs 122 and 124.

The '929 patent does not recognize the possibility that the clinician can be provided the clinical information he seeks in a three dimensional rendering other than one in which the tissue structure is depicted as opaque surfaces. The present inventor has realized that clinically useful three dimensional presentations can be formed in which the tissue is depicted as a semi-transparent or sparsely completed body. Such a depiction, the present inventor has found, will show the extent of tissue structures by the continuity of the pattern of the acoustic texture and anatomical borders of the tissue. Since different tissues will return ultrasonic echoes with distinct and differing frequency spectra, intensity and duration, differing echo characteristics can be used to differentiate tissue types in a three dimensional ultrasonic image. The semi-transparent or sparsely completed tissue structure enables the viewer of the three dimensional depiction to see through the tissue to the internal structure and vasculature of the organ. As FIG. 1 illustrates, the three dimensional rendering of image frame 150a of the three dimensional image sequence 150 is formed by controlling the transparency (opacity) of the two types of image information by means of blood flow opacity control 130 and tissue opacity control 140. Preferably the opacity controls are capable of separately controlling the display opacity of the two types of image information. With the image opacity thus set, a composite three dimensional rendering is formed using both types of image information in their complementary spatial relationships. Thus, for instance the viewer will be able to examine the internal vascular network 126c of the two organs 122,124 and determine the extent of the internal vasculature of each organ in the three dimensional presentation 128. The boundary and extent of each organ is defined by the extent of the illustrated texture of the tissue seen in the three dimensional image. In a preferred embodiment a sequence 150 of three dimensional projection images is formed, each image from the perspective of a different viewing angle, as described in U.S. Pat. No. 5,485,842. By displaying the images of the sequence in rapid succession on a display 100, the viewer can visualize the three dimensional display of the two organs and their internal structures as they appear to rotate in front of the viewer.

Figure 2:
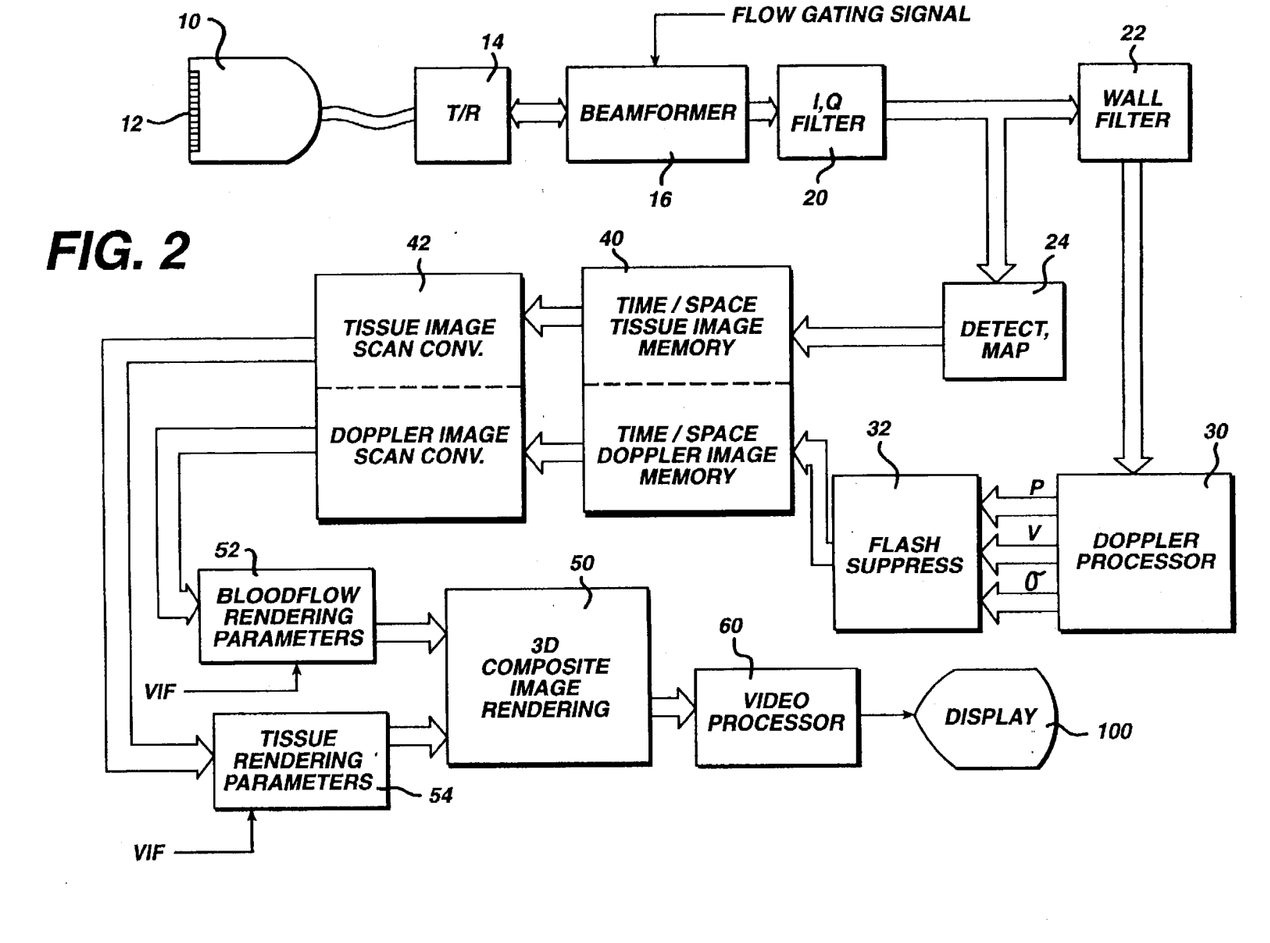
FIG. 2 illustrates in block diagram form an ultrasonic diagnostic imaging system constructed in accordance with the principles of the present invention.

Turning now to FIG. 2, an ultrasonic diagnostic imaging system constructed in accordance with the principles of the present invention is shown in block diagram form. A scanhead 10 includes a transducer array 12 which transmits ultrasonic pulses into a patient and receives back ultrasonic echoes. The transducer array 12 is pulsed and echoes received by a transmitter/receiver 14. Ultrasonic beams transmitted and received by the transducer array are steered and focused under control of a beamformer 16, which processes echo signals from a plurality of elements to form scanlines of coherent echo signals. The received echo signals are quadrature detected and filtered by an I,Q filter 20, then processed for either B mode or Doppler display.

For B mode processing the I and Q samples are coupled to a detector and grayscale mapping circuit 24, which produces grayscale signals with brightness corresponding to the intensity of received echo signals. The grayscale signals are stored in a tissue image memory 40 together with information bearing their spatial relationship to the image field. In a preferred embodiment scanlines of grayscale signals are acquired to form a full planar image, and a sequence of B mode planar tissue images is stored in tissue image memory 40. The image planes retain their spatial orientation to each other by being stored in the time or spatial sequence in which they were acquired.

For Doppler processing the I and Q samples undergo highpass filtering in a wall filter 22, then are assembled in ensembles of Doppler data in a Doppler processor 30. The data ensembles are processed by a Doppler technique such as autocorrelation or Fourier transform processing to produce Doppler signals of parameters such as Doppler power (P), velocity (v), or variance ($\sigma$). The Doppler signals are processed to remove motion artifacts in a flash suppresser 32, then stored in a Doppler image memory together with information bearing their spatial relationship to the image field. In a preferred embodiment scanlines of Doppler signals are acquired to form a full planar image, and a sequence of Doppler images is stored in a Doppler image partition of image memory 40, or a separate memory. The Doppler images retain their spatial orientation to each other by being stored in the time or spatial sequence in which they were acquired. The tissue and Doppler image information is then scan converted into the desired image format, such as a sector format, in a scan converter 42. Separate scan converters may be employed to rapidly scan convert tissue and Doppler images simultaneously, or a single scan converter may be used by time multiplexing the processing of the two types of image information. Scan conversion may also be merged into the rendering operations, whereby the two functions are carried out together (i.e., convert polar coordinate scanlines directly into a rectilinearly addressed three dimensional image.)

The separate tissue and Doppler (blood flow) image information is processed together to render a composite three dimensional presentation. The ultrasound system operator enters rendering parameters into rendering parameter storage areas 52 and 54 by means of a user interface (UIF). These parameters control the manner in which each type of image information will be processed in the rendering. For instance, the user may enter values for the opacity and contrast to be imparted to each type of image information. Preferably the parameters for the two types of image information may be separately determined, so that the different types of image information can be processed differently. This enables, for example, the tissue image information to be displayed with greater transparency than the blood flow information, or with greater or lesser contrast.

Figure 4:
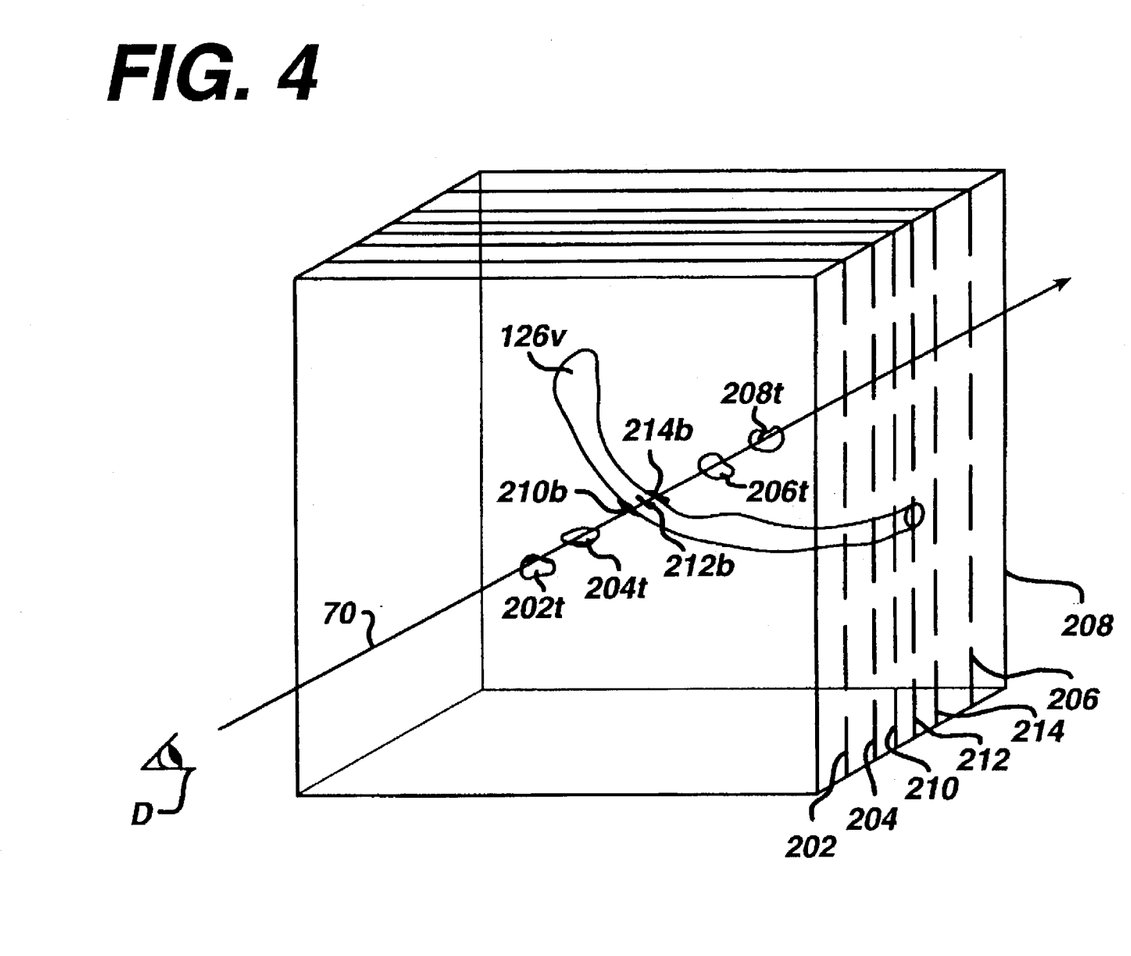
FIG. 4 illustrates the rendering of a pixel of a three dimensional projection image in accordance with the principles of the present invention.

The spatially corresponding tissue and blood flow image information, retaining its depth characteristics, is rendered together in accordance with the rendering parameters to form a three dimensional image presentation in a 3D composite image rendering processor 50. A preferred technique of three dimensional rendering is illustrated by FIG. 4, which depicts a three dimensional overlay of a number of planar blood flow and tissue images 202–214. As described in U.S. Pat. No. 5,485,842, a three dimensional projection image may be formed by combining spatially acquired planar images. In FIG. 4 both tissue and blood flow image information is rendered together by producing a composite pixel from the pixels of the overlaid images which are encountered when vectors along a viewing direction are directed through the images. In this example a vector 70 passes through the image planes in a given direction, encountering tissue information on planes 202, 204, 206, and 208, and blood flow information on planes 210, 212, and 214. The first pixel of information encountered along the vector is a tissue pixel identified as 202t on image plane 202. This pixel is nearest to a viewer D who is observing the three dimensional structure from the origin of the vector 70. The next pixel encountered is tissue pixel 204t on image plane 204. Next, three blood flow pixels of a blood vessel 126v are encountered on image planes 210, 212, and 214. Behind the blood vessel the vector 70 intersects a tissue pixel 206t on image plane 206 and a final tissue pixel 208t on the back image plane 208.

Figure 3:
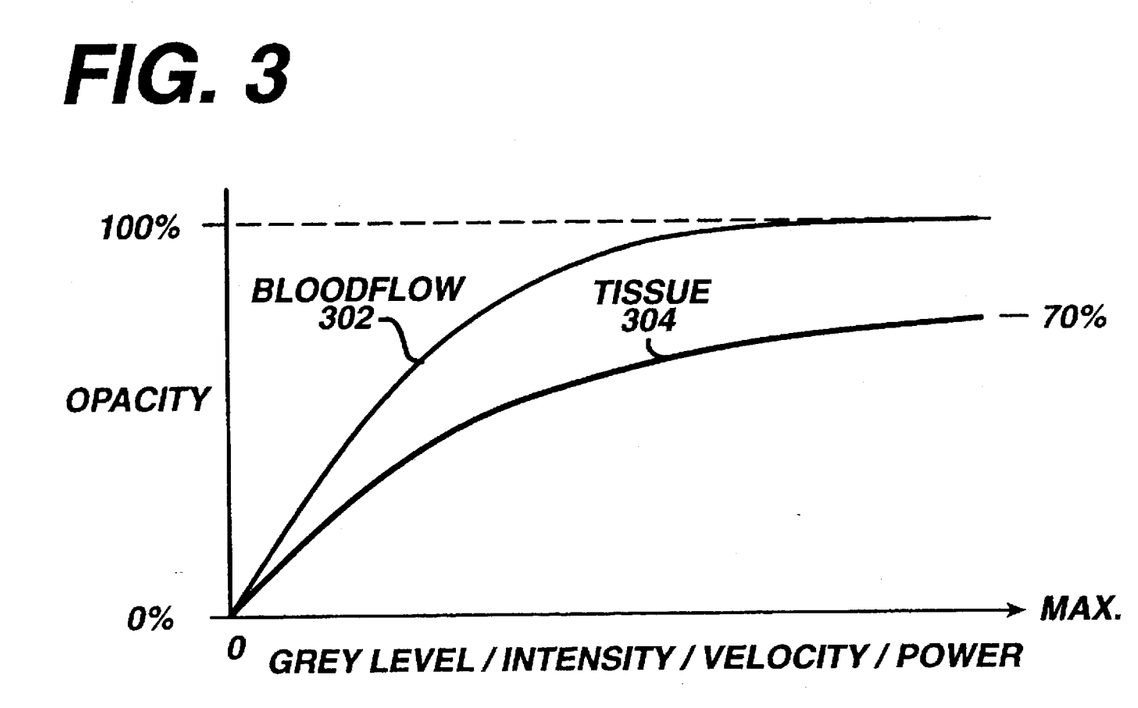
FIG. 3 illustrates the characteristics of separate three dimensional rendering parameters for ultrasonic blood flow and tissue image information.

A single image pixel for display in a three dimensional projection image is produced from this information. It may be seen that, if the tissue pixel 202t is produced as opaque, it will obscure all of the subsequent image information along the vector. Effectively, only the nearest tissue surface will be rendered. But in a preferred embodiment, tissue pixels of a given intensity are given an opacity which is semi transparent, and less than that of a blood flow pixel of the same intensity. Referring to FIG. 3, two curves 302 and 304 are shown of the parameters for opacity control of the blood flow and tissue information, respectively. Curve 302 shows that, as the intensity or velocity or power or grayscale level of the Doppler information signals increases, the degree of opacification of the blood flow pixels increases, reaching a maximum of 100% opacity. The tissue information, however, increases with grayscale level or intensity or power to a maximum opacity of 70% in the example. Thus, tissue pixels will never be fully opaque, but always semi transparent.

The preferred rendering algorithm, in addition to variable opacity weighting, also weights the contributions of the tissue and blood flow information in the three dimensional display by the depth of the image planes in the plane sequence (i.e., in the body). The preferred algorithm is of the form $$P_{3D} = \sum_v a_t a_d P_t + a_b a_d P_b$$

where $P_t$ and $P_b$ are tissue and blood flow pixel values and $a_t$ and $a_b$ are opacity weighting coefficients for tissue and blood flow pixels, and $a_d$ is a depth weighting coefficient. Preferably the weighting coefficients $a_t$ and $a_b$ are functionally variable for each pixel as shown by the curves of FIG. 3, and may additionally or alternatively be functionally related to the spatial location of the pixels, the grayscale or color pixel values, or the relationship of color to grayscale pixel levels or variation. Thus, image information along the vector v can be weighted by opacity and depth to arrive at a composite three dimensional rendering, a result which cannot be attained by separately rendering the tissue and blood flow information, then combining the renderings. All of the pixel information encountered along the vector 70 is weighted and summed in this manner. For instance, the first tissue pixel 202t will have the greatest depth coefficient $a_d$, since it is closest to the viewer D, but will also be weighted by its gray level and will be semi transparent. Its contribution to the final 3D pixel $P_{3D}$ will be determined by these two weighting coefficients. The next tissue pixel 204t will have a lesser depth coefficient than the first pixel 202t, since it is further from the viewer. The following blood flow pixels 201b, 212b, and 214b may have significant opacity weighting coefficients $a_b$ because they are blood flow pixels, but will have lesser depth coefficients $a_d$. When all of the weighted contributions are summed together, the blood flow may still be visible behind the semi transparent tissue pixels, and the 3D pixel $P_{3D}$ could be a light pink color in the three dimensional display, where red signifies blood flow and brightness signifies tissue. The rendered pixel would thus be a depth dependent composite of both characteristics.

Returning to the clinical example given at the outset of this specification, where the placenta is tightly adjacent to the uterine wall, a three dimensional image of these two structures may reveal a stippled image texture in the region of the placenta and a more striated image texture in the region of the uterine wall. Thus, the clinician would be able to determine blood flow in the placenta by that part of the three dimensional vessel structure which is surrounded by a stippled image texture, as compared to vasculature of the uterine wall which is surrounded by a more striated texture. Thus, even without a sharply drawn tissue boundary between the two structures, the clinician is able to assess the vasculature of the placenta under what are usually clinically problematic conditions.

The present three dimensional display technique can be performed with any type of Doppler flow information, such as power Doppler or velocity (color flow) information. While the ultrasonic Doppler and B mode echo information can be obtained by gating the acquisition of both types of information to a phase of the pulsatile flow of blood, it has been found that excellent three dimensional renderings of pulsatile structures may be obtained by utilizing ungated power Doppler signal acquisition and gated B mode acquisition. For instance, if the region being imaged is moving in synchronism with the heartbeat cycle, the tissue information is gathered in synchronism with a flow gating signal such as an ECG heart gate signal. Tissue signal information is thus acquired during a constant phase of the heart cycle. The power Doppler signals, however, need not be gated, but can be acquired at all other times when the tissue signals are not being acquired. Essentially, power Doppler information is acquired as rapidly and often as possible, while tissue information is acquired only at the desired phase of the heart cycle. After the power Doppler information has been temporally averaged, a combined rendering of tissue and blood flow information displays the blood flow information in spatial correspondence with the tissue structure.

Figure 5:
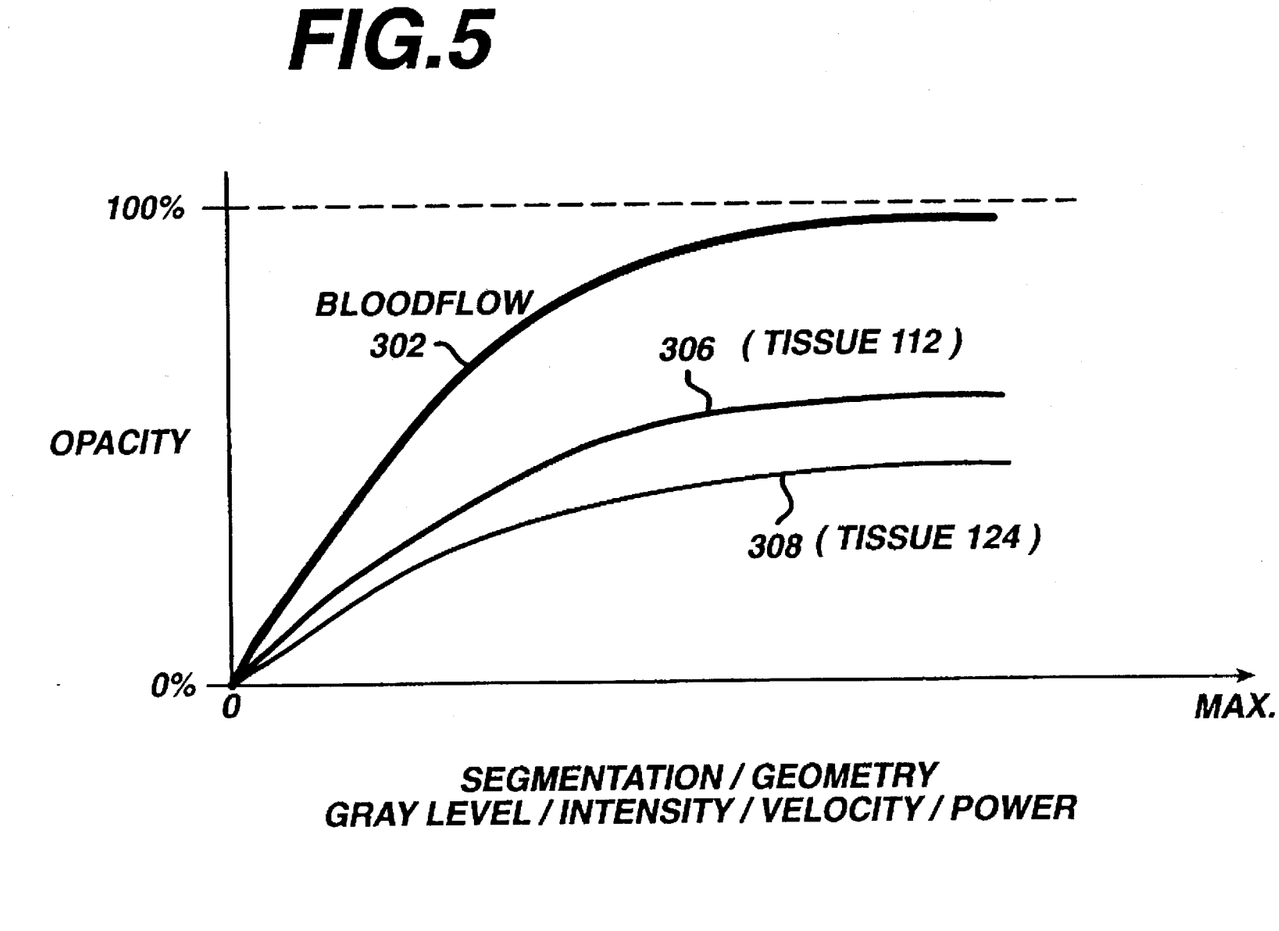
FIG. 5 illustrates opacity versus segmentation.

It may be further appreciated that a semi transparent three dimensional presentation of tissue structure may also be obtained by use of a spatially dependent opacity function in the three dimensional rendering operation. Opacity can be dependent upon a segmentation function, for example. FIG. 5, for instance, illustrates two opacity curves 306,308 which are a function of tissue segmentation or geometry. The curves could correspond to the tissue of organs 122 and 124 in image 120a of FIG. 1, for example. A geometric opacity function can be used which omits tissue information in alternate pixels of a three dimensional rendering to produce a sparsely completed tissue structure. Such a rendering will enable a viewer to seen inside a tissue structure, since the tissue structure will thereby be given a gapped or perforated appearance. The preferred rendering technique of opacity and depth weighting of tissue and blood flow gives a smoother, more pleasing appearance to the three dimensional display presentation.

What is claimed is:

1. A medical diagnostic ultrasound system which develops three dimensional images of flow or motion and structure comprising:

an ultrasonic transducer for receiving ultrasonic echoes from a volumetric region of the body;

an image processor for processing ultrasonic echoes to produce B mode display information of said volumetric region;

a Doppler processor for processing ultrasonic echoes to produce Doppler display information of said volumetric region; and a three dimensional image processor for processing said B mode and said Doppler display information together to render a three dimensional image of both flow or motion and structure in said volumetric region, including separate processing parameters for said B mode and Doppler display information.

2. The medical diagnostic ultrasound system of claim 1, wherein said three dimensional image processor comprises means for processing B mode and Doppler display information together as a function of the relative spatial location of the information.

3. A medical diagnostic ultrasound system which develops three dimensional images of flow or motion and structure comprising:

an ultrasonic transducer for receiving ultrasonic echoes;

an image processor for processing ultrasonic echoes to produce B mode display information;

a Doppler processor for processing ultrasonic echoes to produce Doppler display information; and a three dimensional image processor for processing said B mode and said Doppler display information together to form a three dimensional image, including separate processing parameters for said B mode and Doppler display information, wherein said separate processing parameters comprise a first opacity control parameter for B mode information and a second opacity control parameter for Doppler information.

4. The medical diagnostic ultrasound system of claim 3, wherein said opacity control parameters permit a greater opacity contribution for Doppler information than for B mode information.

5. The medical diagnostic ultrasound system of claim 4, wherein said second opacity control parameter permits a fully opaque maximum opacity level for Doppler information, and said first opacity control parameter permits a semi transparent maximum opacity level for B mode information.

6. A medical diagnostic ultrasound system which develops three dimensional images of flow or motion and structure comprising:

an ultrasonic transducer for receiving ultrasonic echoes;

an image processor for processing ultrasonic echoes to produce B mode display information;

a Doppler processor for processing ultrasonic echoes to produce Doppler display information; and a three dimensional image processor for processing said B mode and said Doppler display information together to form a three dimensional image, including separate processing parameters for said B mode and Doppler display information, wherein said three dimensional image processor comprises means for processing B mode and Doppler display information together as a function of the relative spatial location of the information, and wherein said three dimensional image processor processes B mode and Doppler display information to form three dimensional display pixels $P_{3D}$ in accordance with $$P_{3D} = \sum_{v} a_t a_d P_t + a_b a_d P_b$$

where $P_t$ and $P_b$ are tissue and blood flow pixel information, $a_t$ and $a_b$ are opacity weighting coefficients for tissue and blood flow, $a_d$ is a depth weighting coefficient, and v is a vector of $P_t$ and $P_b$.

7. A medical diagnostic ultrasound system which develops three dimensional images of flow or motion and structure comprising:

an ultrasonic transducer for receiving ultrasonic echoes from a volumetric region;

means for processing ultrasonic echoes to produce B mode display information over said volumetric region;

means for processing ultrasonic echoes to produce Doppler display information from said volumetric region; and rendering means for processing B mode and Doppler display information together as a function of relative location in said volumetric region to form a three dimensional image of said volumetric region in which both flow or motion and structure are visible, including means for separately controlling the opacity of B mode and Doppler information.

8. A medical diagnostic ultrasound system which develops three dimensional images of flow or motion and structure comprising:

an ultrasonic transducer for receiving ultrasonic echoes from a volumetric region;

means for processing ultrasonic echoes to produce B mode display information;

means for processing ultrasonic echoes to produce Doppler display information; and rendering means for processing B mode and Doppler display information together as a function of relative location in said volumetric region to form a three dimensional image, including means for separately controlling the opacity of B mode and Doppler information, wherein said opacity controlling means permits a greater opacity contribution for Doppler information than for B mode information.

9. The medical diagnostic ultrasound system of claim 8, wherein said opacity controlling means permits a fully opaque maximum opacity level for Doppler information, and a semi transparent maximum opacity level for B mode information.

10. A medical diagnostic ultrasound system which develops three dimensional images of flow or motion and structure comprising:

an ultrasonic transducer for receiving ultrasonic echoes from a volumetric region;

means for processing ultrasonic echoes to produce B mode display information;

means for processing ultrasonic echoes to produce Doppler display information; and rendering means for processing B mode and Doppler display information together as a function of relative location in said volumetric region to form a three dimensional image, including means for separately controlling the opacity of B mode and Doppler information, wherein said rendering means comprises means for processing B mode and Doppler display information to form three dimensional display pixel information $P_{3D}$ in accordance with $$P_{3D} = \sum_v a_t a_d P_t + a_b a_d P_b$$

where $P_t$ and $P_b$ are tissue and blood flow pixel information, $a_t$ and $a_b$ are opacity weighting coefficients for tissue and blood flow, $a_d$ is a depth weighting coefficient, and v is a vector of $P_t$ and $P_b$.

11. A method of producing three dimensional ultrasonic images of flow or motion anti structure comprising the steps of:
   a. insonifying a volumetric region of the body with ultrasound;
   b. receiving ultrasonic echo information from said volumetric region;
   c. processing said ultrasonic echo information to produce spatially distinct ultrasonic signals of structure and motion within said volumetric region; and
   d. processing said ultrasonic structure and motion signals together as of function of their spatial properties to render a three dimensional ultrasonic image in which both structure and motion are three dimensionally displayed, including the use of separate rendering parameters for said structure and motion ultrasonic signals.

12. The method of claim 11, wherein said processing of step c comprises
   processing said ultrasonic echo information with a B mode processor and a Doppler processor to produce spatially distinct B mode signals of structure and Doppler signals of motion.

13. A method of producing three dimensional ultrasonic images of flow or motion and structure comprising the steps of:
   a. insonifying a volumetric region of the body with ultrasound:
   b. receiving ultrasonic echo information from said volumetric region:
   c. processing said ultrasonic echo information to produce spatially distinct ultrasonic signals of structure and motion within said volumetric region: and
   d. processing said ultrasonic structure and motion signals together as of function of their spatial properties to render a three dimensional ultrasonic image, including the use of separate rendering parameters for said structure and motion ultrasonic signals,
   wherein said separate rendering parameters of step d comprise separate opacity rendering parameters.

14. The method of claim 13, wherein said separate opacity rendering parameters for said structure and motion ultrasonic signals permit a greater opacity contribution for motion ultrasonic signals than for structure ultrasonic signals.

15. A method of producing dimensional ultrasonic images of flow or motion and structure comprising the steps of:
   a. insonifying a volumetric region of the body with ultrasound;
   b. receiving ultrasonic echo information from said volumetric region;
   c. processing said ultrasonic echo information to produce spatially distinct ultrasonic signals of structure and motion within said volumetric region; and
   d. processing said ultrasonic structure and motion signals together as of function of their spatial properties to render three dimensional ultrasonic image, including the use of separate rendering parameters for said structure and motion ultrasonic signals,
   wherein said processing of said ultrasonic structure and motion signals together comprises forming three dimensional display pixels $P_{3D}$ in accordance with $$P_{3D} = \sum_v a_t a_d P_t + a_b a_d P_b$$

where $P_t$ and $P_b$ are structure and motion pixel information, $a_t$ and $a_b$ are opacity weighting coefficients for structure and motion, $a_d$ is a depth weighting coefficient, and v is a vector of $P_t$ and $P_b$.

16. A method of producing three dimensional ultrasonic images of flow or motion and structure comprising the steps of:
   a. insonifying a volumetric region of the body with ultrasound;
   b. receiving ultrasonic echo information from said volumetric region;
   c. processing said ultrasonic echo information with a B mode processor and a Doppler processor to produce spatially distinct B mode signals of structure and Doppler signals of motion within said volumetric region; and
   d. processing said B mode and Doppler signals together as of function of their spatial properties to render a three dimensional ultrasonic image, including the use of separate opacity rendering parameters for said B mode and Doppler ultrasonic signals which permit a greater opacity contribution for Doppler ultrasonic signals than for B mode ultrasonic signals.

17. A medical diagnostic ultrasound system which develops three dimensional images of pulsatile flow or motion and structure within the body comprising:
   an ultrasonic transducer for receiving ultrasonic echoes from a volumetric region of the body;
   an image processor for processing ultrasonic echoes gated to a phase of the heart cycle to produce B mode display information;
   a Doppler processor for processing ungated ultrasonic echoes to produce Doppler display information; and
   a three dimensional image processor for processing said gated B mode and said ungated Doppler display information as a function of their spatial properties in the volumetric region to form a three dimensional image of both tissue structure and fluid flow within said volumetric region.

18. The medical diagnostic ultrasound system of claim 17, wherein ultrasonic echoes for said Doppler processor are acquired in intervals between the heart gated echoes.

19. The medical diagnostic ultrasound system of claim 17, further comprising means for temporally averaging said Doppler display information.

* * * * *